United States Patent [19]

Klemm et al.

[11] 4,067,982

[45] Jan. 10, 1978

[54] ARYL-SUBSTITUTED PIPERAZINYL-ALKYLAMINO-URACILS, -URACIL ETHERS AND -URACIL THIOETHERS AS THERAPEUTICS

[75] Inventors: Kurt Klemm, Allensbach; Wolfgang Schoetensack, Constance; Wolfgang Prusse, Hegne, all of Germany

[73] Assignee: Byk Gulden, Constance, Germany

[21] Appl. No.: 675,122

[22] Filed: Apr. 8, 1976

Related U.S. Application Data

[62] Division of Ser. No. 65,445, Aug. 20, 1970, Pat. No. 3,957,786.

[51] Int. Cl.$^2$ ............................................ A61K 31/495
[52] U.S. Cl. ................................................... 424/250
[58] Field of Search ......................................... 424/250

*Primary Examiner*—Stanley J. Friedman
*Attorney, Agent, or Firm*—Weiser, Stapler & Spivak

[57] ABSTRACT

Aryl-substituted piperazinyl-alkylamino-uracils, the corresponding uracil ethers and uracil-thioethers and their pharmaceutically acceptable salts such as the hydrochloride, and method for the preparation of these compounds. The novel compounds are useful for lowering the blood pressure, causing an analgesic, a sedative or antihistiminic effect in mammalians.

20 Claims, 2 Drawing Figures

ARYL-SUBSTITUTED PIPERAZINYL-ALKYLAMINO-URACILS, -URACIL ETHERS AND -URACIL THIOETHERS AS THERAPEUTICS

This is a division of application Ser. No. 65,445, filed Aug. 20, 1970, now U.S. Pat. No. 3,957,786.

This invention concerns new aryl-substitute piperazinyl-alkylamino-uracils and the uracil ethers and uracil thioethers corresponding to the general Formula I and their salts with pharmaceutically acceptable acids.

In this and succeeding formulas $R^1$ and $R^2$ each represent hydrogen, a linear or branched, saturated or unsaturated lower alkyl group having up to 6 carbon atoms, or a cycloalkyl or phenyl group;

$R^3$ represents hydrogen, a linear or branched, saturated or unsaturated alkyl, aralkyl, aryl or cycloalkyl group having up to 12, preferably 6 carbon atoms, a halogen atom or a nitro, nitroso, amino, alkylamino, dialkylamino, acylamino, acyl, formyl, ethoxy carbonylamino group, or the thiocyanato group, the -CONHR$^4$ group, wherein $R^4$ is an alkyl group having up to 4 carbon atoms or a phenyl or a substituted phenyl like alkyl-substituted (e.g. lower alkyl up to 4 carbon atoms);

X represents the —NR$^5$- group, wherein $R^5$ is a hydrogen atom or a linear or branched alkyl group having up to 4 carbon atoms or an oxygen or sulfur atom;

A represents a linear or branched, saturated or unsaturated alkylene group having from 1 to 6, preferably 1 to 3, especially 3 carbon atoms.

Y represents a hydrogen atom or an alkyl group having up to 6 carbon atoms, and

Z represents a hydrogen atom or one or more alkyl, alkoxy or mercaptoalkyl groups, the alkyl group having from 1 to 6 carbon atoms, or one or more trifluoromethyl groups or halogen atoms.

The new compounds of the invention are generally, with a few exceptions, crystalline solids, having medium to high melting point. The free base is usually insoluble or difficultly soluble in water; it is usually soluble in chlorinated hydrocarbon solvents, such as chloroform or ether. The new aryl substituted piperazinyl alkyl-mino-uracils are depressants of the nervous system of animals such as vertebrates and mammals and lower the blood pressure of such animals. Their mode of action is different from that of conventional hypertonics.

The new uracil compounds and their pharmaceutically acceptable salts are also useful for administration to animals for studying the behaviour of the animals and for studying drug effects on the central nervous system thereof.

In the attached drawing, Diagrams 1 and 2 demonstrate the lowering of the systolic and diastolic blood pressure in humans by the application of various doses of a typical compound of the invention.

The most preferred aryl-substituted piperazinyl-alkylamino-uracils, -uracil ethers and -uracil thioethers of the invention are those which correspond to the general Formula I including also the salts of these compounds with pharmaceutically acceptable inorganic and organic acids.

In Formula I $R^1$ and $R^2$ each represents a hydrogen atom, a linear, saturated alkyl group having 1 to 4 carbon atoms or a cycloalkyl, the cyclopentyl or cyclohexyl, or a phenyl group the methyl group being most preferred. The cycloalkyl group or phenyl groups can be substituted with lower alkyl like methyl;

$R^3$ represents a hydrogen atom, a linear saturated alkyl group having up to 4 carbon atoms, a halogen atom, preferably chlorine or bromine, a nitro group, a nitroso group, an animo group, an alkylamino group, wherein the alkyl contains 1 to 3 carbon atoms, a dialkylamino group, wherein each of the groups contains 1 to 3 carbon atoms, an acylamino group containing from 1 to 4 carbon atoms, a formyl group, an ethoxycarbonylamino group or a thiocyanato group, wherein those compounds, wherein $R^3$ is hydrogen, a linear saturated alkyl group of 1 to 4 carbon atoms, bromine, an amino group or a diethylamino group are most preferred;

X represents an -NH- group, an —N(C$_2$H$_5$)— group, an oxygen atom or a sulfur atom;

A represents a —CH$_2$—CH$_2$—CH$_2$- group, a —CH(CH$_3$)—CH$_2$— group or a —CH$_2$—CH(CH$_3$)- group, X being in all these cases linked to the left side of the represented group, i.e. A being lined to X and the nitrogen in the ring;

Z represents a hydrogen atom, a methyl group, one or two methoxy groups, one ethoxy group or a chlorine atom, wherein those compounds, wherein Z stands for one methoxy group, preferably in the o-position are most preferred.

The present invention provides furthermore a new method for the preparation of the compounds of the general Formula I above and of the salts of these compounds with pharmacologically acceptable inorganic or organic acids.

The method of the invention comprises several embodiments.

In one embodiment a) of the new method a compound of the general Formula II wherein $R^1$, $R^2$, $R^3$, X and A have the meaning set out hereinbefore in connection with Formula I, and Hal represents a halogen atom, preferably a chlorine or bromine atom is reacted with a phenylpiperazine of the general Formula III or with a salt thereof wherein Y and Z have the meaning set out hereinbefore in connection with general Formula I.

In another embodiment b) of the new method a compound of the general Formula Iv wherein $R^1$, $R^2$, $R^3$, and Hal have the meaning set out hereinbefore in connection with embodiment a) of the method is reacted with a compound of the general Formula V wherein A, X, Y and Z have the meaning set out hereinbefore in connection with Formula I.

Compounds having the general Formula VI wherein $R^1$, $R^2$, A, X, Y and Z have the meaning set out hereinbefore in connection with general Formula I and wherein $R^6$ is a halogen atom or nitroso, amino, alkylamino, dialkylamino, acylamino, acyl, formyl, ethoxycarbonylamino, thiocyanato, or the —CONHR$^4$ group, wherein $R^4$ is defined above, can advantageously be prepared by an embodiment c) of the method of the invention, in which the substituent $R^6$ is introduced by a suitable substitution reaction into the 5-position of a compound of the general Formula VII wherein $R^1$, $R^2$, A, X, Y and Z are defined above in connection with Formula I, to obtain the compounds of Formula I or VI, which can be converted to their salts, if desired.

In a most preferred embodiment of the new method of the invention for the production of the new aryl-substituted piperazinyl-alkylamino-uracils, -uracil ethers and -uracil thioethers by the embodiments (a) and (b) of the method described above, the reaction is effected at a raised temperature, most advantageously between 50° and 150° C. The reaction is preferably carried out in the presence of an inert solution, such as chloroform, benzene, toluene or xylene. Beneficially, an equivalent amount of an auxiliary base, such as triethylamine is added, or, if desired, an excess of the basic starting material of the general Formula III or V, respectively, is used. If the reaction is carried out in the absence of an inert solvent, it is generally advantageous, to work in the presence of an excess of said auxiliary base. In some instances, it is possible to use water as the solvent in the reaction.

In the embodiment (c) of the method of the invention, the various substituents $R^6$ are preferably introduced in the following manner:

1. The halogen atom is introduced by halogenation of the compounds of the general Formula VII, preferably by treatment of the compound with elemental halogen, such as chlorine or bromine, under halogenation conditions.

2. The alkylamino group is introduced by reaction of the halogen substituted product, obtained by the foregoing embodiment 1 of the method, with the desired alkylamine.

3. The dialkylamino group is introduced by reaction of the halogen substituted product, obtained by the foregoing embodiment 1 of the method, with the desired dialkylamine.

4. The acyl group is introduced by reaction of the compounds of the general Formula VII with an acylation agent containing the desired acyl group, such as the corresponding aliphatic or aromatic carboxylic acid anhydride or the corresponding carboxylic acid halide.

5. The —CONHR$^4$ group is introduced by the reaction of the compounds of the general Formula VII with the corresponding isocyanate.

6. The nitroso group is introduced by treatment of the compounds of the general Formula VII with a compound, which yields under reaction conditions the nitroso group, such a i-amylnitrite.

7. The amino group is introduced by reduction of the nitroso group in the nitroso compounds, produced by the foregoing embodiment 6 of the method, e.g. by the reaction with dithionite.

8. The acylamino group may be introduced by acylation of the amino group in the amino substituted compounds, obtained by the foregoing embodiment 7 of the method, by treatment with the desired acylation agent, for instance, with the corresponding aliphatic or aromatic carboxylic acid anhydride or carboxylic acid halide containing the respective acyl radical.

9. The ethoxycarbonylamino group is introduced by reacting acylamino substituted compounds obtained by the foregoing embodiment 8 of the method, with a chloroformic acid ester.

10. The formyl group is introduced by reacting the compounds of the general Formula VII with acetic acid-formic acid anhydride.

11. The thiocyanato group is introduced by treatment of the compounds of the general Formula VII with a compound yielding under reaction conditions a thiocyanato group, such as ammonium thiocyanate in the presence of bromine.

The most preferred method of the invention for the production of the compounds of the general Formula I above and of their salts with pharmacologically acceptable inorganic or organic acids comprises:

a. Reacting a compound of the general Formula II wherein $R^1$, $R^2$, $R^3$, A and X have the significance set out hereinbefore in connection with the general Formula I of the most preferred compounds and wherein Hal is a chlorine or bromine atom with a phenylpiperazine of the general Formula III or with a salt thereof wherein Z has the significance set out hereinbefore in connection with the general Formula I, of the most preferred compounds or b. Reacting a compound of the general Formula IV wherein $R^1$, $R^2$, $R^3$ and Hal have the significance set out hereinbefore, in connection with general Formula II, with a compound of the general Formula V wherein A, X and Z have the significance set out hereinbefore in connection with general preferred Formula I.

Compounds having the general Formula VI wherein $R^1$, $R^2$, A, X and Z have the meaning set out hereinbefore in connection with the preferred general Formula I and wherein $R^6$ is a halogen atom, a nitroso group, an amino group, an alkylamino group having up to 3 carbon atoms, a dialkylamino group having up to 6 carbon atoms, an acylamino group having up to 4 carbon atoms, a formyl group, an ethoxy carbonylamino group or a thiocyanato group, those compounds being most preferred wherein $R^6$, is a bromine atom, an amino group or a diethylamino group, are most advantageously prepared by embodiment c) of the new method of the invention is which the substituent $R^6$ is introduced by a suitable substitution reaction into the 5-position of a compound corresponding to the general Formula VII wherein $R^1$, $R^2$, A, X and Z have the significance set out hereinbefore in connection with the preferred general Formula I, to obtain the compounds of Formula I or VI, which can be converted to their respective salts, if desired.

The new compounds of the invention, especially as prepared by embodiments a, b, c, a, b, c of the new method, are, if desired, converted into their pharmacologically acceptable salts by contacting and reacting the free based with the corresponding, desired pharmacologically acceptable inorganic acid or organic acid.

The production of the pharmacologically acceptable salts of the compounds of the general Formula I may be effected by dissolving the free base in a suitable solvent and reacting the dissolved base by the addition of the required amoutn, usually the equivalent amount of the desired acid and recovering the salt of the compound. For the production of the difficulty soluble salts of the base, it is possible to use for the reaction with the acid, instead of the free base, a soluble salt thereof. In the case of difficultly soluble acids, it is often beneficial to use a soluble salt of the acid for the reaction.

Suitable organic and inorganic acids comprise for instance, acetic acid, oxalic acid, maleic acid, fumaric acid, tartaric acid, benzoic acid, pamoic acid, salicylic acid, polygalacturonic acids, polyvinylcarboxylic acids, hydrochloric acid, sulfuric acid, phosphoric acid, amido sulfonic acid, methane sulfonic acid. Hydrochloric acid and sulfuric aci are generally the mos preferred acids for the formation of the pharmacologically acceptable salts.

In similar manner, the free base of the uracil compounds of the invention may be produced from the corresponding salt of the compound by hydrolysis, e.g. by adding at least a molar equivalent of sodium hydroxide or other suitable strong base in aqueous solution, followed by extraction or separation of the free base in usual manner.

As disclosed above, the invention comprises salts of the new uracil compounds, which are readily soluble in water and salts which are difficultly soluble in water, whereby the salts of lesser solubility in water are especially useful for the retard forms of the compounds of the invention.

Typical compounds of the invention include those described below including those in Table I which shows melting points and yields of the compounds illustrated in the examples.

In the reaction of the invention in embodiment a), it is desirable for best yields to use the reactants of formula II and III in a mole ratio of 1 to 2.2 to about 2.5, respectively and in embodiment b) the reactants of formula IV and V in a mole ratio of 1 to 2.2 to 2.5, respectively. In embodiment c) the reactants are desirably used in a 1 to 1 mole ratio, with the base in a 10 to 20 time excess.

Table I

Compounds of Examples 1 to 43

| Compound of Example No. | R¹ | R² | R³ | X | A | Y | Z | Melting Point C[1] | Yield % |
|---|---|---|---|---|---|---|---|---|---|
| 1 | $CH_3$ | $CH_3$ | H | NH | $-CH_2-CH_2-CH_2-$ | H | p-$CH_3$ | 175 | 74 |
| 2 | $CH_3$ | $CH_3$ | H | NH | $-CH_2-CH_2-CH_2-$ | H | o-Cl | 150 | 45 |
| 3 | $CH_3$ | $CH_3$ | H | NH | $-CH_2-CH_2-CH_2-$ | H | 2,5-di-$OCH_3$ | 195 | 52 |
| 4 | $CH_3$ | $CH_3$ | H | NH | $-CH_2-CH_2-CH_2-$ | H | o-$OC_2H_5$ | 174 | 65 |
| 5 | $CH_3$ | $CH_3$ | H | NH | $-CH_2-CH_2-CH_2-$ | H | 2,4-di-$OCH_3$ | 121 | 72 |
| 6 | $CH_3$ | $CH_3$ | H | NH | $-CH_2-CH_2-CH_2-$ | H | 2,4-di-$OCH_3$ | 121 | 72 |
| 7 | $CH_3$ | $CH_3$ | H | NH | $-CH_2-CH_2-CH_2-$ | H | m-$OCH_3$ | 148 | 70 |
| 8 | $CH_3$ | $CH_3$ | H | NH | $-CH_2-CH_2-CH_2-$ | H | p-$OCH_3$ | 155 | 60 |
| 9 | $CH_3$ | $CH_3$ | N | O | $-CH_2-CH_2-CH_2-$ | H | o-$OCH_3$ | 146 | 58/88 |
| 10 | $CH_3$ | $CH_3$ | H | NH | $-CH_2-CH_2-$ | H | o-$OCH_3$ | 169 | 80 |
| 11 | $CH_3$ | $CH_3$ | H | NH | $-CH_2-CH_2-CH_2-H$ | H | 114 | 63 | |
| 12 | $CH_3$ | $CH_3$ | H | NH | $-CH_2-CH_2-CH_2-$ | H | o-$CH_3$ | 162 | 72 |
| 13 | $CH_3$ | $CH_3$ | H | NH | $-CH_2-CH_2-CH_2-$ | H | p-Cl | 178 | 46 |
| 14 | $CH_3$ | $CH_3$ | $CH_3$ | NH | $-CH_2-CH_2-CH_2-$ | H | o-$OCH_3$ | 120 | 66 |
| 15 | $CH_3$ | $CH_3$ | n-$C_4H_9$ | NH | $-CH_2-CH_2-CH_2-$ | H | o-$OCH_3$ | Base oil[2][3] | 54[2] |
| 16 | $CH_3$ | $CH_3$ | $NO_2$ | NH | $-CH_2-CH_2-CH_2-$ | H | o-$OCH_3$ | 162 | 82 |
| 17 | $CH_3$ | $CH_3$ | H | NH | $-CH-CH-$<br>$\quad\ \ \|$<br>$\quad\ \ CH_3$ | H | o-$OCH_3$ | 166 | 51 |
| 18 | $CH_3$ | $CH_3$ | B4 | NH | $-CH_2-CH$ hd 2$-CH_2-$ | H | o-$OCH_3$ | 197[10] | 56 |
| 19 | $CH_3$ | $CH_3$ | NO | NH | $-CH_2-CH_2-CH_2-$ | H | o-$OCH_3$ | ca.125 | 77 |
| 20 | $CH_3$ | $CH_3$ | $NH_2$ | NH | $-CH_2-CH_2-CH_2-$ | H | o-$OCH_3$ | 123 | 79 |
| 21 | $CH_3$ | $CH_3$ | $NHCOC_2H_5$ | NH | $-CH_2-CH_2-CH_2-$ | H | o-$OCH_3$ | 132 | 84 |
| 22 | $CH_3$ | H | H | NH | $-CH_2-CH_2-CH_2-$ | H | o-$OCH_3$ | 232 | 41 |
| 23 | $CH_3$ | $CH_3$ | H | NH | $CH_3$<br>$\ \|$<br>$-CH-CH_2-$ | H | o-$OCH_3$ | 238[9] | |
| 24 | $C_6H_{11}$ | H | H | NH | $-CH_2-Ch_2-CH_2-$ | H | o-$OCH_3$ | 218 | 38 |
| 25 | $C_6H_{11}$ | H | $C_4H_9$ | NH | $-CH_2-CH_2-CH_2-$ | H | o-$OCH_3$ | 155 | 66 |
| 25 | $C_4H_9$ | H | H | NH | $-CH_2-CH_2-CH_2-$ | H | o-$OCH_3$ | 204 | 50 |
| 25 | H | H | H | NH | $-CH_2-CH_2-CH_2-$ | H | o-$OCH_3$ | 270 | 30 |
| 26 | $CH_3$ | $CH_3$ | CH=O | NH | $-CH_2-CH_2-CH_2-$ | H | o-OCH | 122 | 40 |
| 27 | $CH_3$ | $CH_3$ | $NHCOOC_2H_5$ | NH | $-CH_2-CH_2-CH_2-$ | H | o-$OCH_3$ | 125 | 60 |
| 28 | $CH_3$ | $CH_3$ | SCN | NH | $-CH_2-CH_2-CH_2-$ | H | o-$OCH_3$ | 188 | 80 |
| 29 | $C_6H_5$ | H | H | NH | $-CH_2-CH$ hd 2$-CH_2-$ | H | o-$OCH_3$ | 186 | 80 |
| 30 | H | $C_6H_5$ | H | NH | $-CH_2-CH_2-CH_2-$ | H | o-$OCH_3$ | 218 | 18 |
| 31 | $CH_3$ | $CH_3$ | $N(C_2H_5)_2$ | NH | $-CH_2-CH_2-CH_2-$ | H | o-OCH | oil[4] | 46 |
| 32 | $CH_3$ | $CH_3$ | $CONHC_6H_5$ | NH | $-CH_2-CH_2-CH_2-$ | H | o-$OCH_3$ | 165[5] | 81 |
| 33 | $CH_3$ | $CH_3$ | $COCH_3$ | NH | $-CH_2-CH_2-CH_2-$ | H | o-$OCH_3$ | 98 | 40 |
| 34 | $CH_3$ | $CH_3$ | H | $N(C_2H_5)$ | $-CH_2-CH$ hd 2$-CH_2-$ | H | o-$OCH_3$ | 162[6] | 75 |
| 35 | $CH_3$ | $CH_3$ | H | O | $-CH_2-CH_2-CH_2-$ | H | o-$OCH_3$ | oil[7] | 78 |
| 36 | $CH_3$ | $CH_3$ | H | O | $-CHCH_2-$<br>$\ \|$<br>$\ CH_3$ | H | H | oil[8] | 49 |
| 37 | $CH_3$ | $CH_3$ | H | O | $-CHCH_2-$<br>$\ \|$<br>$\ CH_3$ | H | p-$CH_3$ | 120 | 70 |
| 38 | $CH_3$ | $CH_3$ | H | 0 | $-CHCH_2-$<br>$\ \|$<br>$\ CH_3$ | H | p-Cl | 163 | 80 |
| 39 | $CH_3$ | $CH_3$ | H | S | $-CH-CH_2-$<br>$\quad\ \ \|$<br>$\quad\ \ CH_3$ | H | o-$OCH_3$ | 148 | 78 |
| 40 | $CH_3$ | $CH_3$ | H | S | $-CH-CH_2-$<br>$\quad\ \ \|$<br>$\quad\ \ CH_3$ | H | H | 230[9] | 59 |
| 41 | $CH_3$ | $CH_3$ | H | S | $-CH-CH_2-$<br>$\quad\ \ \|$<br>$\quad\ \ CH_3$ | H | m-$CH_3$ | 217[9] | 48 |
| 42 | $CH_3$ | $CH_3$ | H | S | $-CH-CH_2-$<br>$\quad\ \ \|$<br>$\quad\ \ CH_3$ | H | p-$CH_3$ | 152 | 45 |

Table I-continued
Compounds of Examples 1 to 43

| Compound of Example No. | R¹ | R² | R³ | X | A | Y | Z | Melting Point C[1] | Yield % |
|---|---|---|---|---|---|---|---|---|---|
| 43 | $CH_3$ | $CH_3$ | H | S | $-CH-CH_2-$<br>$\quad\;\;\mid$<br>$\quad\;\;CH_3$ | H | p-Cl | 152 | 28 |

Remarks to Table I
[1] = Melting point of the free base, unless noted otherwise
[2] = Picrate has melting point of 173 – 175° C
[3] = Oxalate has melting point of 155° C Dioxalate has melting point of 173° C Trihydrochloride has melting point of 192° C
[4] = Trihydrochloride × 1 $H_2O$ has melting point of 231° C
[5] = Hydrochloride has melting point of 225° C
[6] = Dihydrochloride sinters at 162° C and above
[7] = Dihydrochloride has melting point of 220° C
[8] = Dihydrochloride sinters at 170° C and above
[9] = Dihydrochloride
[10] = Dihydrobromide Further illustrative compounds of the invention include the following.

EXAMPLE 2

| Example | R¹ | R² | R³ | X | A | Y | Z |
|---|---|---|---|---|---|---|---|
| 44 | butyl | methyl | H | NH | $-(CH_2)_3-$ | H | p-$CH_3$ |
| 45 | methyl | hexyl | H | NH | $-(CH_2)_2-$ | H | o-Cl |
| 46 | ethyl | methyl | H | NH | $-(CH_2)_2-$ | H | o-$OCH_2CH_3$ |
| 47 | methyl | isopropyl | H | NH | $-(CH_2)_2-$ | H | o-$CH_2CH_3$ |
| 48 | methyl | pentyl | H | NH | $-(CH_2)_2-$ | H | o-CF |
| 49 | methyl | methyl | benzyl | NH | $-(CH_2)_2-$ | H | o-Br |
| 50 | methyl | methyl | phenyl | NH | $-(CH_2)_2-$ | 2-$CH_3$ | p-$C_3$ |
| 51 | methyl | methyl | OCH— | NH | $-(CH_2)_2-$ | H | p-$CH_3$ |
| 52 | methyl | methyl | $NHCOOC_3H_7$ | NH | $-(CH_2)_2-$ | H | p-$CH_3$ |
| 53 | methyl | methyl | $N(C_3H_7)_2$ | NH | $-(CH_2)_2-$ | H | p-$CH_3$ |
| 54 | isopropyl | H | H | NH | $-(CH_2)_4-$ | 3-$CH_2-CH_3$ | p-$CH_3$ |
| 55 | allyl | methyl | H | NH | $-(CH_2)_3-$ | 2-$(CH_3)_2-CH_2-$ | p-$CH_3$ |
| 56 | propenyl | methyl | H | NH | $-(CH_2)_3-$ | 3-$(CH_3)_2-CH_2-$ | p-$CH_3$ |
| 57 | methyl | isobutyl | H | O | $-(CH_2)_3-$ | 2-$CH_3$ | p-$CH_3$ |
| 58 | ethyl | H | H | NH | $-C_2CH:CH-$ | H | H |
| 59 | methyl | methyl | H | $N(CH_3)$ | $-(CH_2)_3-H$ | H | |
| 60 | methyl | H | allyl | NH | $-(CH_2)_3-$ | H | p-Cl |
| 61 | methyl | methyl | NO | NH | $-(CH_2)_3-$ | H | o-$CH_3$ |

The following examples illustrate the invention, but are not to be construed as limiting the same.

EXAMPLE 1

1,3-Dimethyl-4-(γ-[4-(p-tolyl)-piperazinyl-(1)]-propylamino)-uracil 26 g (0.11 mole) of p-tolylpiperazinecarbonate and 12 g (0.05 mole) of 1,3-dimethyl-4-(γ-chloropropylamino)-uracil were dissolved in 150 ml ethanol. After the addition of 200 ml toluene, the ethanol was distilled off, and the mixture was boiled under reflux for 2 hours and filtered while still hot. The solvent was removed from the filtrate in vacuo and the residue boiled with ether and filtered. The residue thus obtained was thereafter furthur purified by recrystallization from an acetone solution in a Thielepape device. The recrystallization may also be effected from a methanol solution.

11 g of 1,3-dimethyl-4-(γ-[4-(p-tolyl)-piperazinyl-(1)]-propylamino)-uracil, having a melting point of 174°–175° C, were obtained, corresponding to a yield of 74%.

1,3-Dimethyl-4-(γ-[4-(o-chlorophenyl)-piperazinyl-(1)]-propylamino)-uracil 11.6 g (0.05 mole) of 1,3-dimethyl-4-(γ-chloropropylamino)-uracil and 34 g (0.15 mole) of o-chlorophenylpiperazine-carbonate were boiled for 3 hours in 350 ml xylene under reflux. After cooling the mixture, 200 ml 6n sodium hydroxide solution were added and the separated aqueous phase extracted with chloroform. The chloroform extract and the xylene phase were thereafter combined, dried over magnesium sulfate, filtered and the solvents evaporated. The brown residue was then purified chromatographically in a column of silica gel "neutral", (Merck A.G.) having a particle size of 0.05–0.2 mm. The flow agent was a mixture of ethyl acetate, methanol and concentrated aqueous ammonia in a ratio of 20:4:1. The light brown material thus obtained was recrystallized from methanol with the addition of activated carbon. 8.5 g of 1,3-dimethyl-4-(γ-[4-(o-chlorophenyl)-piperazinyl-(1)]-propylamino)-uracil, having a melting point of 150°–151° C, were thus obtained, representing a yield of 45%.

EXAMPLE 3

1,3-Dimethyl-4-(γ-[4-(2,5-dimethoxyphenyl)-piperazinyl-(1)]-propylamino)-uracil 29.5 g (0.1 mole) of the dihydrochloride of 2,5-dimethoxyphenyl-piperazine were dissolved in water, and the solution was made alkaline by the addition of sufficient 6 n aqueous sodium hydroxide. The solution was then extracted with chloroform and the chloroform evaporated from the extract. To the free base thus obtained were added 11.6 g (0.05 mole) of 1,3-dimethyl-4-(-chloropropylamino)-uracil and 500 ml xylene. The mixture was heated for 2 hours under reflux and the xylene distilled off in vacuo. The residue was purified chromatographically in a column of silica gel "neutral" (Merck A.G.) with the use of a mixture of ethyl acetate, methanol and concentrated aqueous ammonia in a ratio of 20:4:1 as the flow agent. The purification may also be effected by recrystallization from methanol, preferable with the use of the Thielepape device.

11 g of 1,3-dimethyl-4-(γ-[4-(2,5-dimethoxyphenyl)-piperazinyl-(1)]-propylamino)-uracil having a melting point of 194°–195° C were obtained, representing a yield of 52%.

EXAMPLE 4

1,3-Dimethyl-4-(γ-[4-(o-methoxyphenyl)piperazinyl-(1)]-propylamino)-uracil a. 28.2 g (0.11 mole) of o-methoxyphenylpiperazine-carbonate and 11.6 g (0.05 mole) of 1,3-dimethyl-4-(γ-chloropropylamino)-uracil were boiled under reflux for 5 hours in 150 ml water. The cooled aqueous solution was made alkaline by the addition of sufficient 6 n aqueous sodium hydroxide and extracted with chloroform. The chloroform extract was dried and the chloroform evaporated. The residue was crystallized from 200 ml ether and the crystalline phase was filtered off by suction. 14.8 g 1,3-dimethyl-4-(γ-[4-(o-methoxyphenyl)-piperazinyl-(1)]-propylamino)-uracil, having a melting point of 156° C, were obtained, representing a yield of 77%.

The product was obtained in similarly good yield by the extraction of the aqueous reaction mixture with hot toluene and precipitation of the compound from the toluene solution by the addition of petroleum ether (boiling in the range from 50°–70° C.).

b. 600 g (2.36 moles) of o-methoxyphenylpiperazine-carbonate were dissolved with stirring and heating in 3 l xylene, with the evolution of carbon dioxide. A solution of 242 g (1.04 mole) 1,3-dimethyl-4-(γ-chloropropylamino)-uracil in 1.5 l methanol was then added drop by drop, while maintaining the temperature of the xylene solution at 120° C, whereby the methanol continuously distilled off. After completion of the addition of the methanol solution, the reaction mixture was heated to and stirred at 140° C for one more hour, whereafter the solution, while still at this temperature, was filtered by suction to separate the o-methoxyphenyl-piperazine hydrochloride precipitated during the reaction. The filter residue was washed with hot xylene.

312 g of a brown reaction product (representing 81% yield) were recovered by cooling the filtrate, filtering off the precipitate by suction, concentrating the filtrate thus obtained by partial evaporation, cooling again and filtering by suction the additional quantities of precipitate.

The raw product was purified by recrystallization from ethanol with the addition of activated carbon to result in 280 g 1,3-dimethyl-4-(γ-[4-(o-methoxyphenyl)-piperazinyl-(1)]-propylamino)-uracil of a melting point of 156° C corresponding to a yield of 70%.

Purification of the raw product by boiling in acetone resulted in similar yields.

c. 20.6 g (0.083 mole) of N-(o-methoxyphenyl)-N'-(3-aminopropyl)-piperazine and 15.7 g (0.09 mole) of 1,3-dimethyl-4-chlorouracil were boiled for 15 hours in 100 ml triethylamine. The excess triethylamine was then distilled off in vacuo and the residue was dissolved in 300 ml 1n hydrochloric acid with subsequent filtration. The filtrate thus obtained was cooled with ice and 2 n aqueous ammonic solution was slowly added with stirring. As soon as the first precipitation appeared, a few crystals of the desired product were added to the solution. The ammoniacal suspension was stirred for one more hour, the precipitate filtered off by suction and washed with 200 ml water. The material was purified by recrystallization from ethanol with the addition of activated carbon. In this manner 24.2 g 1,3-dimethyl-4-(γ-[4-(o-methoxyphenyl)-piperazinyl(1)]-propylamino)-uracil having a melting point of 156° C were obtained corresponding to a yield of 75%. The purification may also be effected by boiling the material in acetone to result in similar yields.

The new compounds described in the following Examples 5 to 8 were produced by the methods described in the preceding examples 3 and 4b with the substitution of the correspondingly substituted starting materials.

EXAMPLE 5

1,3-Dimethyl-4-(γ[4-(o-ethoxyphenyl)-piperazinyl-(1)]-propylamino)-uracil was prepared in a yield of 65% and the compound had a melting point of 173°–174° C.

EXAMPLE 6

1,3-Dimethyl-4-(γ-[4-(2,4-dimethoxyphenyl)-piperazinyl-(1)]-propylamino)-uracil was prepared in a yield of 72% and had a melting point of 120°–122° C.

EXAMPLE 7

1,3-Dimethyl-4-(γ-[4-(m-methoxyphenyl)-piperazinyl-(1)]-propylamino)-uracil was prepared in a yield of 70% and had a melting point of 147°–148° C.

EXAMPLE 8

1,3-Dimethyl-4-(γ-[4-(p-methoxyphenyl)-piperazinyl-(1)]-propylamino)-uracil was prepared in a yield of 60% and had a melting point of 155°–156° C.

EXAMPLE 9

1,3-Dimethyl-4-(γ-[4-(o-methoxyphenyl)-piperazinyl-(1)]-propyloxy)-uracil a. 3.1 g (0.011 mole) of 1,3-dimethyl-4-(γ-bromopropyloxy)-uracil and 6.7 g (0.03 mole) of o-methoxyphenylpiperazinecarbonate were heated for 3 hours in 100 ml xylene under reflux. The solution was then cooled and the precipitated hydrobromide of the o-methoxyphenylpiperazine was filtered off and washed with benzene. The solvent was distilled off in vacuo from the filtrate and the residue was taken up for the subsequent chromatography in a small quantity of a flow agent consisting of a mixture of ethyl acetate, methanol and concentrated aqueous ammonia in a ratio of 20:4:1. The chromatography was effected in 280 g silica gel "neutral" (Merck A.G.), having a particle size of 0.05 to 0.2 mm. In this manner, 3.8 g 1,3-dimethyl-4-(γ-[4-(o-methoxyphenyl)-piperazinyl-(1)]-propyloxy)-uracil were obtained, representing a yield of 88%. Recrystallized from ethyl acetate, the compound had a melting point of 146°–148° C.

b. 3.5 g of a 33% dispersion of sodium metal in toluene (containing about 0.05 mole sodium) were diluted with 35 ml of absolutely dry toluene and 9.5 g (0.035 mole) of N-(o-methoxyphenyl)-N'-(γ-hydroxypropyl)-piperazine were added thereto with stirring. When the violent exothermic reaction had subsided, 8.8 g (0.05 mole) of 1,3-dimethyl-4-chloro-uracil were added in small portions to the reaction mixture at room temperature. Thereby a thick suspension was formed, which was heated with reflux for 1.5 hours. After cooling, 80 ml 2 n hydrochloric acid were added, and the mixture was extracted three times with 25 ml benzene each time for the removal of unreacted chlorouracil. Thereafter, the $P_H$ was adjusted to 8 by the addition of 1 n aqueous sodium hydroxide and the mixture extracted three times with 100 ml chloroform each. The chloroform extracts were combined and dried and the chloroform evaporated. The residue was recrystallized from ethanol to result in 8.3 g of 1,3-dimethyl-4-(γ-[4-(o-methoxyphenyl)piperazinyl-(1)]-propyloxy)-uracil having a melting point of 145°–148° C and representing a yield of 58%.

EXAMPLE 10

1,3-Dimethyl-4-(β-[4-(o-methoxyphenyl)-piperazinyl-(1)-]-ethylamino)-uracil 6.6 g (0.03 mole) of 1,3-dimethyl-4-(β-chloroethylamino)-uracil and 15.6 g (0.07 mole) of o-methoxyphenyl-piperazine carbonate were heated for 2 hours in 200 ml xylene with reflux. To the cooled reaction mixture were added 150 ml 6 n aqueous sodium hydroxide, and the organic phase was separated. The aqueous alkaline phase was extracted with chloroform. The organic phases were combined, dried over magnesium sulfate and the organic solvent evaporated in vacuo. The residue was briefly boiled with ether, and the crystals thus formed were filtered off and recrystallized from acetone.

9 g 1,3-dimethyl-4-(β-[4-(o-methoxyphenyl)piperazinyl-(1)]-ethylamino)-uracil are obtained, having a melting point of 169° C and representing a yield of 80%.

EXAMPLE 11

1,3-Dimethyl-4-(γ-[4-phenyl-piperazinyl-(1)]-propylamino)-uracil 25 g (0.14 mole) of 1,3-dimethyl-4-chlorouracil, 31.4 g (0.14 mole) of N'-phenyl-N-(3-aminopropyl)-piperazine and 50 ml of triethylamine were boiled with reflux for 16 hours in 150 ml chloroform. For the removal of unreacted chloro-uracil, the chloroform and triethylamine were evaporated in vacuo, the residue dissolved in 200 ml chloroform and the solution thus obtained was extracted twice with 10 ml each of 2 n hydrochloric acid. To the combined aqueous extracts were added 100 ml of 6 n aqueous sodium hydroxide and the solution extracted twice with chloroform. The combined chloroform extracts were freed from chloroform and the residue was crystallized by rubbing in the presence of ether. The crystals were recrystallized from 150 ml ethyl acetate to result in 32 g of 1,3-dimethyl-4-(γ-[4-phenyl-piperazinyl-(1)]-propylamino)-uracil, having a melting point of 114° C and representing a yield of 63%.

EXAMPLE 12

1,3-Dimethyl-4-(γ-[4-(o-tolyl)-piperazinyl(1)]-propylamino)-uracil

A mixture of 5.3 g (0.03 mole) of 1,3-dimethyl-4-chlorouracil and 7.0 g (0.03 mole) of N-(o-tolyl)-N'-(3-aminopropyl)-piperazine in 10 ml triethylamine were boiled for 10 minutes with reflux. The excess triethylamine was then removed in vacuo and the residue dissolved in 70 ml chloroform. The solution was then extracted three times with 40 ml each of 2 n hydrochloric acid. The combined aqueous-acid phases were then made alkaline by the addition of 40 ml 6 n aqueous sodium hydroxide and extracted with chloroform. The chloroform extract was dried and the chloroform evaporated, leaving 11 g of an oil, which soon thereafter crystallized. After recrystallization from benzene, 8.1 g of 1,3-dimethyl-4-(γ-[4-(o-tolyl)-piperazinyl-(1)]propylamino)-uracil were obtained, having a melting point of 162° C and representing a yield of 72%.

EXAMPLE 13

1,3-Dimethyl-4-(γ-[4-(p-chlorophenyl)-piperazinyl-(1)]-propylamino)-uracil 3.1 g (0.017 mole) of 1,3-dimethyl-4-chlorouracil, 4.3 g (0.017 mole) of N-(p-chlorophenyl)-N'-(γ-aminopropyl)-piperazine and 10 ml triethylamine were heated for 1.5 hours with reflux. The excess triethylamine was then removed in vacuo and the residue was dissolved in 50 ml chloroform. The chloroform solution was extracted three times with 50 ml each of 2 n hydrochloric acid. The combined acid phases were washed with chloroform, made alkaline with 6 n aqueous sodium hydroxide and extracted three times with 50 ml each of chloroform. The chloroform extracts were combined, dried and the chloroform evaporated. The residue thus obtained amounted to 5.9 g. After recrystallization from ethanol, 3.3 g of 1,3-dimethyl-4-(γ-[4-(p-chlorophenyl)-piperazinyl-(1)]-propyl-amino)-uracil, having a melting point of 178°–179° C were obtained, representing a yield of 46%.

EXAMPLE 14

1,3,5-Trimethyl-4-(γ-[4-(o-methoxyphenyl)-piperazinyl-(1)]-propylamino)-uracil 5.6 g (0.03 mole) of 1,3,5-trimethyl-4-chlorouracil and 17.5 g (0.07 mole) of N-(o-methoxyphenyl)-N'(γ-aminopropyl)-piperazine were boiled for 30 hours in 70 ml xylene with reflux. The N-(o-methoxyphenyl)-N'-(γ-aminopropyl)-piperazine hydrochloride crystallizing upon cooling of the reaction mixture, was filtered off and washed with hot benzene. The filtrate was freed from the solvent in vacuo and the residue chromatographically purified in a stationary column of 350 g silica gel "neutral" (Merck A.G.) of a particle size of 0.05 to 0.2 mm with the use of a mixture of 10 parts chloroform and 1 part ethanol as the flow agent. 8 g of 1,3,5-trimethyl-4-(γ-[4-(o-methoxyphenyl)-piperazinyl-(1)]-propylamino)-uracil, having a melting point of 120°–121° C were obtained, representing a yield of 66%.

EXAMPLE 15

1,3-Dimethyl-4-(γ-[4-(o-methoxyphenyl)-piperazinyl-(1)]-propylamino)-5-n-butyl-uracil 7.0 g (0.03 mole) of 1,3-dimethyl-4-chloro-5-n-butyl-uracil and 17.5 g (0.07 mole) of N-(o-methoxyphenyl)-N'(γ-aminopropyl)-piperazine were boiled in 70 ml xylene for 5 days with reflux. The hydrochloride of the N-(o-methoxyphenyl)-N'-(γ-aminopropyl)-piperazine, crystallizing upon cooling of the reaction mixture, was filtered off by suction and the filtrate was evaporated. The residue was chromatographically purified in a stationary column of silica gel "neutral" (Merck A.G.) of a particle size of 0.02 to 0.5 mm, with the use of a mixture of 10 parts chloroform and 1 part ethanol as the flow agent. In this manner, 11.4 g of a brown oil were obtained, which was taken up in 250 ml benzene. After addition of a saturated solution of picric acid in benzene, the precipitate formed thereby was permitted to settle and the benzene was decanted. The solid residue was recrystallized from ethanol by help of a Thielepape device. In this manner 11 g of the picrate of 1,3-dimethyl-4-(γ-[4-(o-methoxyphenyl)-piperazinyl-(1)]-propylamino)-5-n-butyl-uracil, having a melting point of 173°–175° C were obtained, corresponding to a yield of 54%.

EXAMPLE 16

1,3-dimethyl-4-(γ-[4-(o-methoxyphenyl)-piperazinyl-(1)]-propylamino)-5-nitro-uracil To a solution of 11 g (0.05 mole) of 1,3-dimethyl-4-chloro-5-nitro-uracil in 150 ml benzene was added drop by drop at room temperature and with stirring a solution of 32 g (0.1 mole) of N-(o-methoxyphenyl)-N'-(γ-aminopropyl)-piperazine. At first a hard to stir precipitate was formed, which dissolved after completion of the addition of the second solution. Thereafter, the hydrochloride of the piperazine compound precipitated in crystalline form. The reaction mixture was then boiled for about 15 minutes and filtered after cooling. The filtrate was evaporated and the residue recrystallized from alcohol.

17.7 g of 1,3-dimethyl-4-(γ-[4-(o-methoxyphenyl)-piperazinyl-(1)]-propylamino-5-nitrouracil, having a melting point of 160°–162° C were obtained, representing a yield of 82%.

EXAMPLE 17

1,3-Dimethyl-4-(β-[4-(o-methoxyphenyl)-piperazinyl-(1)]-propylamino)-uracil

A mixture of 4 g (0.023 mole) of 1,3-dimethyl-4-chloro-uracil and 12 g (0.046 mole) of 1-amino-2-[4-(o-methoxyphenyl)-piperazinyl-(1)]-propane was boiled for 5 hours in 300 ml xylene with reflux. After cooling, the precipitate was filtered off and washed with hot benzene. The combines filtrate and washings were evaporated in vacuo and chromatographically purified in a column of silica gel "neutral" (Merck A.G.) of a particle size of 0.05–0.2 mm. The flow agent was a mixture of ethyl acetate, methanol and concentrated aqueous ammonia in a ratio of 20:4:1. The brown product thus obtained (5.5 g) was recrystallized from 70 ml ethylacetate in the presence of activated carbon.

4.5 g of 1,3-dimethyl-4-(β-[4-(o-methoxyphenyl)-piperazinyl-(1)]-propylamino)-uracil, having a melting point of 165°–166° C were obtained, representing a yield of 51%.

EXAMPLE 18

1,3-Dimethyl-4-(γ-[4-(o-methoxyphenyl)-piperazinyl-(1)]-propylamino)-5-bromo-uracil-dihydrobomide 10 g (0.026 mole) of 1,3-dimethyl-4-(γ-[4-(o-methoxyphenyl)-piperazinyl-(1)]-propylamino)-uracil were dissolved in 30 ml glacial acetic acid and a mixture of 4.5 g bromine in 30 ml glacial acetic acid was added drop by drop at 0° C and with stirring within 30 minutes. After stirring the reaction mixture for 30 additional minutes, the crystalline precipitate was filtered off by suction and washed with a mixture of glacial acetic acid and ether. 9.2 g of 1,3-dimethyl-4-(γ-[4-(o-methoxyphenyl)-piperazinyl-(1)-]-propylamino)-5-bromouracil-dihydrobromide having a melting point of 196°–199° C were obtained, representing a yield of 56%.

EXAMPLE 19

1,3-Dimethyl-4-(γ-[4-(o-methoxyphenyl)-piperazinyl-(1)]-propylamino)-5-nitroso-uracil Into the solution of 7.7 g (0.02 mole) of 1,3-dimethyl-4-(γ-[4-(o-methoxyphenyl)-piperazinyl-(1)]-propylamino)-uracil and 6 ml i-amylnitrite in 100 ml of a 1:1 mixture of chloroform and acetone were added drop by drop with cooling by ice 20 ml of a saturated solution of hydrochloric acid in ethanol. The white precipitate, formed in the red solution, was filtered off by suction and washed with acetone. The solid product thus obtained was hygroscopic and recrystallized from methanol to result in 9 g of 1,3-dimethyl-4-(γ-[4-(o-methoxyphenyl)-piperazinyl-(1)]-propylamino)-5-nitroso-uracil in the form of the trihydrochloride containing 3 moles of crystal water. The product decomposes at 165° C. The yield was 77%.

EXAMPLE 20

1,3-Dimethyl-4-(γ-[4-(o-methoxyphenyl)-piperazinyl-(1)]-propylamino)-5-amino-uracil 6.1 g (0.012 mole) of 1,3-dimethyl-4-(γ-[4-(o-methoxyphenyl)-piperazinyl-(1)]-propylamino)-5-nitroso-uracil trihydrochloride were dissolved in 30 ml ice water and a solution of 6 g sodiumdithionite in 30 ml ice water was thereto and the mixture stirred at 0° C for 10 minutes. The yellow, clear solution was underlaid with 50 ml chloroform and the solution was made alkaline by the addition of sufficient ice cooled 6 n aqueous sodium hydroxide. Care was taken thereby, that the temperature did not rise above +3° C. The phases were separated, the chloroform phase was dried and the chloroform evaporated at room temperature in a rotary evaporator.

The residue was crystallized by the addition of ether and filtered off by suction. 3.7 g of 1,3-dimethyl-4-(γ-[4-(o-methoxyphenyl)-piperazinyl-(1)]-propylamino-5-amino-uracil, having a melting point of 122°–124° C, were obtained, representing a yield of 79%. The solid substance decomposed.

EXAMPLE 21

1,3-Dimethyl-4-(γ-[4-(o-methoxyphenyl)-piperazinyl-(1)]-propylamino)-5-propionylamino-uracil To 15 ml propionic acid anhydride were added in small portions at room temperature with stirring 5 g (0.0125 mole) of 1,3-dimethyl-4-(γ-[4-(o-methoxyphenyl)-piperazinyl-(1)]-propylamino)-5-amino-uracil. After several minutes, crystals formed in the clear solution. The reaction mixture was then diluted with 150 ml ether and the precipitate was filtered off by suction. The filter residue was purified in a column of 300 g silica gel "neutral" (Merck A.G.) with the use of a mixture of ethyl acetate, methanol and concentrated aqueous ammonia in a ratio of 20:4:1 by volume. Thereafter, the solvent was completely evaporated from the eluted mixture in a rotary evaporator and the residue recrystallized from 25 ml ethyl acetate. 4.8 g of 1,3-dimethyl-4-(γ-[4-(o-methoxyphenyl)-piperazinyl-(1)]-propylamino)-5-propionylamino-uracil, having a melting point of 132°–133° C were obtained, representing a yield of 84%.

EXAMPLE 22

1-Methyl-4-(γ-[4-(o-methoxyphenyl)-piperazinyl-(1)]-propylamino)-uracil

A mixture of 4.8 g (0.03 mole) of 1-methyl-4-chlorouracil and 15 g (0.06 mole) of γ-[4-(o-methoxyphenyl)-piperazinyl-(1)]-propylamine was heated for 24 hours at 90°14 100° C. The clear solution solidified after cooling to a glass-like mass, which was boiled with the addition of 150 ml ethanol to dissolve the solid mass. Thereafter, the crystals formed in the solution were filtered off by suction, while still hot. The filter residue was washed with ethanol. 4.6 g 1-methyl-4-(γ-[4-(o-methoxyphenyl)-piperazinyl-(1)]-propylamino)-uracil, having a melting point of 230°–233° C, were obtained, representing a yield of 41%.

EXAMPLE 23

1,3-Dimethyl-4-(β-[4-(o-methoxyphenyl)-piperazinyl-(1)]-α-methylethylamino)-uracil A mixture of 6 g (0.024 mole) of N-(o-methoxyphenyl)-N'-(2-aminopropyl)-piperazine, 4.4 g (0.025 mole) of 1,3-dimethyl-4-chloro-uracil and 30 ml triethylamine was boiled for 5 hours with reflux without regard to undissolved material. Thereafter, the triethylamine was removed in vacuo, and 60 ml 2 n aqueous hydrochloric acid added to the residue, followed by extraction with chloroform. The aqueous acid phase was then made alkaline by the addition of 2 n aqueous sodium hydroxide, followed by extraction with chloroform. The residue obtained by removal of the chloroform from the chloroform extract, was purified chromatographically in a column of silica gel "neutral" with the use of a mixture of 5 parts by volume ethyl acetate and 1 part by volume methanol as the flow agent.

In this manner, 2.6 g of an oil, which solidified to a glass-like mass, were obtained, representing a yield of 34%. The hydrochloride of the compound, which had the above composition, was recrystallized in a superheated steam extractor with acetone and found to have a melting point of 238°–240° C.

EXAMPLE 24

1-Cyclohexyl-4-(γ-[4-(o-methoxyphenyl)-piperazinyl-(1)]-propylamino)-uracil

A mixture of 3.4 g (0.015 mole) of 1-cyclohexyl-4-chloro-uracil and 10 g (0.04 mole) of N-(o-methoxyphenyl)-N'-(γ-aminopropyl)-piperazine was heated for 8 hours to a temperature of about 120° C. The cooled reaction mixture was then shaken with 100 ml 2n aqueous hydrochloric acid and 100 ml chloroform; the chloroform phase was discarded. The aqueous, acid solution was thereafter made alkaline, while cooling with ice, by the addition of sufficient 2n aqueous sodium hydroxide and extracted with chloroform. The residue obtained, after evaporation of the chloroform, was purified chromatographically in a column of silica gel "neutral", with the use of a mixture of 6 parts by volume chloroform and 1 part by volume ethanol as the flow agent.

2.5 g 1-cyclohexyl-4-(γ-[4-(o-methoxyphenyl)-piperazinyl-(1)]-propylamino)-uracil were obtained, representing a yield of 38%. The compound was recrystallized from a mixture of 30 ml chloroform and 100 ml ethanol and concentration of the solution by evaporation to 50 ml. The substance had a melting point of 217°–219° C.

EXAMPLE 25

1-n-Butyl-4-(γ-[4-(o-methoxyphenyl)-piperazinyl-(1)]-propylamino)-uracil

A mixture of 8.2 g (0.04 mole) of 1-butyl-4-chlorouracil and 20 g (0.08 mole) N-(o-methoxyphenyl)-N'-(γ-aminopropyl)-piperazine was heated for 3 hours to 140° C. After cooling, the reaction mass was dissolved in chloroform and water. The chloroform phase was separated, evaporated, and the residue recrystallized in a superheated steam extraction from methanol.

8.3 g 1-n-butyl-4-(γ-[4-(o-methoxyphenyl)-piperazinyl-(1)]-propylamino)-uracil, having a melting point of 204° C were obtained, representing a yield of 50%. The following substances were made by following generally the method described in the foregoing example 25, but substituting the correspondingly substituted starting materials: 1-cyclohexyl-4-(γ-[4-(o-methoxyphenyl)-piperazinyl-(1)]-propylamino)-5-n-butyl-uracil was obtained in a yield of 66% and had a melting point of 155° c.

4-(γ-[4-(o-methoxyphenyl)-piperazinyl-(1)]-propylamino-uracil was obtained in a yield of 30% and had a decomposition point of about 270° C.

EXAMPLE 26

1,3-Dimethyl-4-(γ-[4-(o-methoxyphenyl)-piperazinyl-(1)]-propylamino-5-formyl-uracil To 50 ml acetic acid anhydride, cooled to 0° C, were added drop by drop 25 ml formic acid (98–100%). The mixture was then heated for 15 minutes to 50° C and thereafter quickly cooled to 0° C.

12.5 g (0.032 mole) of 1,3-dimethyl-4-(γ-[4-(o-methoxyphenyl)-piperazinyl-(1)]-propylamino)-uracil were then incorporated into the formylation mixture with heating to 100° C for 6 hours. The reaction mixture was then cooled and evaporated at 50°–60° C in vacuo until dry. The residue was then dissolved in water, made alkaline by the addition of 2 n aqueous sodium hydroxide and the solution extracted with chloroform. The chloroform extract was dried with sodium sulfate and the solvent removed by evaporation. The residue was purified chromatographically in a column of silica gel (Merck A.G.) with the use of a mixture of $CHCl_3$ and $C_2H_5OH$ in a ratio of 6:1 by volume.

In this manner 4.9 g of 1,3-dimethyl-4-(γ-[4-(o-methoxyphenyl)-piperazinyl-(1)]-propylamino)-5-formyl-uracil, having a melting point of 122° C were obtained, representing a yield of 97%.

EXAMPLE 27

1,3-Dimethyl-4-(γ-[4-(o-methoxyphenyl)-piperazinyl-(1)]-propylamino)-5-carbethoxyamino-uracil To the solution of 2 g (0.05 mole) of 1,3-dimethyl-4-(γ-[4-(o-methoxyphenyl)-piperazinyl-(1)]-propylamino)-5-amino-uracil in 10 ml chloroform was added drop by drop, at room temperature, the solution of 0.5 ml (0.05 mole) chlorocarbonic acid ester in 5 ml chloroform. After 15 minutes, the reaction mixture was washed with saturated aqueous sodium bicarbonate solution and the organic phase was separated, dried and the solvent evaporated. The residue thus obtained was crystallized by the addition of acetone and filtered off by suction. In this manner, 1.4 g 1,3-dimethyl-4-(γ-[4-(o-methoxyphenol)-piperazinyl-(1)]-propylamino)-5-carbethoxyamino-uracil were obtained, representing a yield of 60%. After recrystallization from acetone, the substance had a melting point of 125° C.

EXAMPLE 28

1,3-Dimethyl-4-(γ-[4-(o-methoxyphenyl)-piperazinyl-(1)]-propylamino)-5-thiocyanato-uracil 50.5 g (0.14 mole) 1,3-dimethyl-4-(γ-[4-(o-methoxyphenyl)-piperazinyl-(1)]-propylamino-uracil and 7.6 g (0.1 mole) ammonium thiocyanate were dissolved in 100 ml glacial acetic acid. The solution was cooled to and held at 10° C, while 40 ml 1 n bromine solution in glacial acetic acid were added dropwise. After completion of the bromine addition, the mixture was stirred for 30 minutes and the precipitate, formed in the reaction, was filtered off by suction and washed with glacial acetic acid and ether. The filtrate was evaporated at 40° C in vacuo until dry and to the residue, thus obtained, was given CHCl$_3$, H$_2$O and concentrated aqueous ammonia. The organic phase was separated and concentrated by evaporation at 40° C in vacuo. After the addition of double the volume of ethanol and renewed evaporation of the solvent, 14.2 g of a precipitate were obtained upon cooling, representing a yield of 80% of 1,3-dimethyl-4-(γ-[4-(o-methoxyphenyl)-piperazinyl-(1)]-propylamino)-5-thiocyanato-uracil, which had a melting point of 188° C.

EXAMPLE 29

1-Phenyl-4-(γ-[4-(o-methoxyphenyl)-piperazinyl-(1)]-propylamino)-uracil

A mixture of 6.7 g (0.03 mole) 1-phenyl-4-chlorouracil and 18 g (0.072 mole) N-(o-methoxyphenyl)-N'-(γ-aminopropyl)-piperazine was heated for one half hour at 150° C. The cooled reaction mixture was then stirred for 1 hour with 100 ml water and 100 ml chloroform with subsequent separation of the phases. The chloroform phase was dried and the solvent evaporated. The residue thus obtained was purified chromatographically in a column of 360 g silica gel "neutral" (Merck A.G.) of a particle size of 0.05 to 0.2 mm. The flow agent was a mixture of chloroform and ethanol in a ratio of 6:1 by volume.

10.4 g 1-phenyl-4-(γ-[4-(o-methoxyphenyl)-piperazinyl-(1)]-propylamino)-uracil, corresponding to a yield of 80%, were obtained. The substance, recrystallized from ethanol, had a melting point of 186° C.

EXAMPLE 30

3-Phenyl-4-(γ-[4-(o-methoxyphenyl)-piperazinyl-(1)]-propylamino)-uracil

A mixture of 11.2 g (0.05 mole) 3-phenyl-4-chlorouracil and 27.5 g (0.11 mole) N-(o-methoxyphenyl)-N'-(γ-aminopropyl)-piperazine was heated for 1 hour at 160° C. The reaction mixture was cooled and dissolved in about 200 ml chloroform and about 200 ml water. The organic phase was separated and the solvent evaporated. The residue was worked up chromatographically in a column of silica gel "neutral" (Merck A.G.) having a particle size of 0.05 to 0.2 mm. The flow agent used was a mixture of chloroform and ethanol in a ratio of 6:1 by volume. 4 g of 3-phenyl-4-(γ-[4-(o-methoxyphenyl)-piperazinyl-(1)]-propylamino)-uracil were obtained as the fastest passing substance, representing a yield of 18%. The substance was recrystallized from ethanol and had a melting point of 218° C.

EXAMPLE 31

1,3-Dimethyl-4-(γ-[4-(o-methoxyphenyl)-piperazinyl-(1)]-propylamino)-5-diethylamino-uracil To a solution of 10 g (0.026 mole) 1,3-dimethyl-4-(γ-[4-(o-methoxyphenyl)-piperazinyl-(1)]-propylamino-uracil (see Example 4) in 60 ml chloroform was added drop by drop at 0° C and within 2 hours a solution of 4.5 g (0.028 mole) bromine in 28 ml chloroform. The reaction mixture was permitted to sit overnight at room temperature, whereafter 20 ml diethylamine were added, followed by boiling under reflux for 2 hours. The cooled mixture was then extracted with water, the remaining organic phase was dried and the solvent evaporated. The residue was purified chromatographically in a column of silica gel "neutral" (Merck A.G.) of a particle size of 0.05 to 0.02 mm. The flow agent was a mixture of chloroform and methanol in a ratio of 40:1 by volume. In this manner, 5.5 g 1,3-dimethyl-4-(γ-[4-(o-methoxyphenyl)-piperzainyl-(1)]-propylamino)-5-diethylamino-uracil were obtained as a light yellow oil, representing a yield of 46%. The trihydrochloride of this compound was obtained with one mole of crystallization and had a melting point of 231° C.

EXAMPLE 32

1,3-Dimethyl-4-(γ-[4-(o-methoxyphenyl)-piperazinyl-(1)]-propylamino)-uracil-5-carbonic acid anilide 3.6 g (0.03 mole) phenylisocyanate were added drop by drop at room temperature to the suspension of 10 g (0.026 mole) 1,3-dimethyl-4-(γ-[4-(o-methoxyphenyl)-piperazinyl-(1)]-propylamino)-uracil (see Example 4) in 100 ml toluene and subsequently boiled under reflux for 9 hours. The solvent was then distilled off and the residue boiled out with ethanol for purification. 10.8 g 1,3-dimethyl-4-(γ-[4-(o-methoxyphenyl)-piperazinyl-(1)]-propylamino)-uracil-5-carbonic acid anilide were obtained as the undissolved residue, having a melting point of 165° C and representing a yield of 81%.

EXAMPLE 33

1,3-Dimethyl-4-(γ-[4-(o-methoxyphenyl)-piperazinyl-(1)]-propylamino)-5-acetyl-uracil 10 g (0.026 mole) 1,3-dimethyl-4-(γ-[4-(o-methoxyphenyl)-piperazinyl-(1)]-propylamino)-uracil (see Example 4) were heated with 30 ml acetic acid anhydride for 5 hours at 50°-60° C. Thereafter, 70 ml ethanol were added to the brown solution and the solvents were evaporated in vacuo. The addition of ether to the residue resulted in crystallization of the starting material, which was filtered off. The ether was then distilled off from the filtrate and the residue chromatographically purified in a column of silica gel "neutral" (Merck A.G.) of a particle size of 0.05–0.2 mm. The flow agent was a mixture of ethyl acetate, methanol and concentrated aqueous ammonia in a ratio of 20:4:1.

In this manner, 4.5 g of an oil were obtained, which had the above stated composition and which represents a yield of 40%. The oil could be crystallized by the addition of ether. Recrystallized from cyclohexane it had a melting point of 97°–98° C.

EXAMPLE 34

1,3-Diemethyl-4-[N-ethyl-N-(γ-[4-(o-methoxyphenyl)-piperazinyl-(1)]-propyl)-amino]-uracil A mixture of 3.5 g (0.02 mole) of 1,3-dimethyl-4-chlorouracil and 9 g (0.032 mole) N-(o-methoxyphenyl-N'-(γ-ethylaminopropyl)-piperazine was heated for ½ hour at 120° C. The reaction product was subject to column chromatographic separation, resulting in 5 g of an oil having the above stated composition and representing 75% yield calculated as the reacted quantity of the starting materials. The oil was converted into the dihydrochloride of the base by contacting it with a solution of HCl in ethanol. The dihydrochloride compound was then recrystallized from isopropanol and found to decompose at a temperature beginning at 162° C.

EXAMPLE 35

1,3-Dimethyl-4-(1-methyl-2-[4-(o-methoxyphenyl)-piperazinyl-(1)]-ethyloxy)-uracil-dihydrochloride 2.5 g (0.1 mole) N-(o-methoxyphenyl)-N'-(2-hydroxypropyl)-piperazine in 150 ml absolute toluene were boiled under reflux for 0.5–1 hour with 5.3 g (0.12 mole) of a 55% sodium hydride suspension in oil. To the cooled reaction mixture were added 19.2 g (0.11 mole) 1,3-dimethyl-4-chloro-uracil with subsequent boiling under reflux for 0.5–1 hour. The reaction product was cooled and washed with water and, after separation, the toluene was evaporated from the toluene solution. The residue was dissolved in 300 ml acetone and the dihydrochloride of the desired compound was precipitated by the addition of ethanol saturated with HCl.

36 g 1,3-dimethyl-4-(1-methyl-2-[4-(o-methoxyphenyl)-piperazinyl-(1)]-ethyloxy)-uracil-dihydrochloride having a melting point of 220° C, were obtained representing a yield of 78%.

EXAMPLE 36

1,3-Dimethyl-4-(1-methyl-2-[4-phenyl-piperazinyl-(1)]-ethoxy)-uracil-dihydrochloride Using N-phenyl-N'-(2-hydroxypropyl)-piperazine as the starting material the method of Example 35 produced 1,3-dimethyl-4-(1-methyl-2-[4-phenyl-piperazinyl-(1)]-ethoxy)-uracil in form of an oil in a yield of 49%. The oil was converted by contact with HCl into the corresponding dihydrochloride, which sintered at 170° C.

EXAMPLE 37

1,3-Dimethyl-4-(1-methyl-2-[4(p-methylphenyl)-piperazinyl-(1)]-ethoxy)-uracil

Using N-(p-methylphenyl)-N'-(2-hydroxypropyl)-piperazine as the starting material in the method of Example 35, 1,3-dimethyl-4-(1-methyl-2-[4-methylphenyl)-piperazinyl-(1)]-ethyloxy)-uracil was obtained in a yield of 70%. The substance had a melting point of 120° C.

EXAMPLE 38

1,3-Dimethyl-4-(1-methyl-2-[4-(p-chlorophenyl)-piperazinyl-(1)]-ethyloxy)-uracil Using in the method of Example 35 N-(p-chlorophenyl)-N'-(2-hydroxypropyl)-piperazine as the starting material, 1,3-dimethyl-4-(1-methyl-2-[4-(p-chlorophenyl)-piperazinyl-(1)]-ethyloxy)-uracil, having a melting point of 163° C, was obtained in a yield of 80%.

EXAMPLE 39

1,3-Dimethyl-4-(1-methyl-2-[4-(o-methoxyphenyl)-piperazinyl-(1)]-ethylthio)-uracil A mixture of 33.5 g (0.15 mole)o-methoxyphenyl-piperazine carbonate and 22 g (0.3 mole) propylenesulfide was boiled under reflux for 1 hour in 100 ml methanol. Excess propylenesulfide was subsequently removed in vacuo. The residue was dissolved in a solution of 5.6 g (0.1 mole) potassium hydroxide in 100 ml methanol and the methanol evaporated in vacuo. By treating the dry residue with acetone at room temperature, the hygroscopic potassium salt of the mercapto compound was isolated.

9.5 g (0.31 mole) of this mercapto compound were heated on the steam bath for 2 hours with 5 g (0.028 mole) of 1,3-dimethyl-4-chlorouracil. Of the two phases, the heavier one solidified upon cooling. The aqueous solution was decanted and the residue was twice recrystallized from methanol. In this manner 9.8 g 1,3-dimethyl-4-(1-methyl-2-[4-(omethoxyphenyl)-piperazinyl-(1)]-ethylthio)uracil, having a melting point of 148° C, were obtained, representing a yield of 78% calculated on the basis of the 1,3-dimethyl-4-chlorouracil starting material.

EXAMPLE 40

1,3-Dimethyl-4-(1-methyl-2-[4-(o-methoxyphenyl)-piperazinyl-(1)]-ethylthio)-uracil Using in the method of Example 39 phenylpiperazine carbonate as the starting material, 1,3dimethyl-40(1-methyl-2-[4-phenyl-piperazinyl-(1)]-ethylthio)uracil was obtained in a yield of 59%. The dihydrochloride of this compound had a melting point of 230° C.

EXAMPLE 41

1,3-Dimethyl-4-(1-methyl-2-[4-(m-tolyl-piperazinyl-(1)]-ethylthio)-uracil-dihydrochloride When m-tolylpiperazine carbonate was used as the starting material in the method of Example 39, 1,3-dimethyl-4-(1-methyl-2-[4-(m-tolyl)-piperazinyl(1]-ethylthio)-uracil was obtained in a yield of 48%. The dihydrochloride of this compound had a melting point of 217° C.

EXAMPLE 42

1,3-Dimethyl-4-(1-methyl-2-[4-(p-tolyl)piperazinyl-(1)]-ethylthio)-uracil

Using in the method of Example 39 p-tolylpiperazine carbonate as the starting material, 1,3-dimethyl-4-(1-methyl-2-[4-(p-tolyl-piperazinyl-(1)]-ethylthio)-uracil, having a melting point of 152° C, was obtained in a yield of 45%.

EXAMPLE 43

1,3-Dimethyl-4-(1-methyl-2-[4-(p-chloro-phenyl)-piperazinyl-(1)]-ethylthio)-uracil Substituting in the method of Example 39 p-chlorophenyl-piperazine carbonate as the starting material, 1,3-dimethyl-4-(1-methyl-2-[4-p-chlorophenyl-piperazinyl-(1)]-ethylthio)-uracil, having a melting point of 152° C, was obtained in a yield of 28%.

1,3-Dimethyl-4-($\gamma$-chloropropylamino)-uracil, which was used as the starting material in Examples 1, 2, 3, 4a, 4b, 5, 6, 7 and 8, may be produced as follows:

210 g (1.2 mole) 1,3-dimethyl-4-chlorouracil were gradually added to 225 g (3 moles) 3-aminopropanol at 100° C. After completion of the reaction, in which the temperature increased to 150° C, the reaction mixture was cooled to 110° C and 200 ml water were added, whereafter the mixture was cooled to 0° C. The precipitated crystalline material was filtered off by suction and washed with ice water and thereafter with acetone and dried over night in a vacuum drying oven at 60° C. 228 g 1,3-dimethyl-4-($\gamma$-hydroxypropylamino)-uracil, having a melting point of 140°-143° C, were obtained, representing a yield of 90%.

To the suspension of 180 g (0.85 mole) 1,3-dimethyl-4-($\gamma$-hydroxypropylamino)-uracil in 800 ml toluene were added dropwise with stirring 155 ml (2.55 moles) thionylchloride. The reaction mixture was cooled sufficiently to prevent that the temperature exceeded 50° C. When the violent evolution of gas subsided, the mixture was gradually heated to 100° C, until the formation of gas came nearly to an end. Thereafter, exces thionylchloride was distilled off in vacuo and the precipitate was filtered off by suction and washed with benzene. The compound was recrystallized from methanol. 167 g 1,3-dimethyl-4-($\beta$-chloro-propylamino)-uracil, having a melting point of 151°-153° C were obtained, representing a yield of 85%.

1,3-Dimethyl-4-($\beta$-chloroethylamino)-uracil, which was used as the starting material in Example 10, was produced in a manner similar to that described above. Substituting in the foregoing method 1,3-dimethyl-4-($\beta$-hydroxy-ethylamino)-uracil, which is described by Goldner and Carstens in Liebigs Annalen 691, 142 (1966), for the 1,3-dimethyl-4-($\beta$-chloroethylamino)-uracil, having a melting point of 203° C, was obtained in a yield of 74%.

1,3-Dimethyl-4-($\beta$-chloroethylamino)-uracil was also produced by the following method:

To an ice cooled suspension of 20 g (0.1 mole) 1,3-dimethyl-4-($\beta$-hydroxyethylamino)-uracil in 300 ml chloroform and 16 ml dimethylformamid was added dropwise a mixture of 16 ml thionylchloride and 40 ml chloroform. The reaction mixture was stirred for two hours with cooling by ice and for an additional 10 hours at room temperature. To the dark red, clear solution thus obtained, was added ice water and sodium bicarbonate solution, and the organic chloroform phase separated from the aqueous phase. The chloroform phase was dried and the chloroform evaporated. The residue was recrystallized from methanol. In this manner — and with further recovery from the mother liquor — 16.1 g 1,3-dimethyl-4-($\beta$-chloroethylamino)-uracil, having a melting point of about 203° C, were obtained, representing a yield of 74%.

1,3-Dimethyl-4-chloro-5-nitro-uracil used in Example 16 as the starting material is described in the Literature by Pfleiderer, Ber. 99. 2997 (1966).

1,3-Dimethyl-4-($\gamma$-bromo-propyloxy)-uracil used in Example 9a as the starting material may be produced by the following method:

Equivalent amounts of 1,3-dimethyl barbituric acid and silver nitrate were mixed in form of their aqueous solutions to produce the silver salt of the 1,3-dimethyl barbituric acid, which precipitated practically quantitatively from the solution. 10.4 g (0.04 mole) of this silver salt were added to 40 g (0.2 mole) 1,3-dibromo-propane in 200 ml benzene. The mixture was boiled for 90 minutes with reflux, cooled, filtered and the benzene evaporated from the filtrate. The residue was purified chromatographically in a column of 350 g silica gel "neutral" (Merck A.G.) having a particle size of 0.05 to 0.2 mm. The flow agent was a mixture of ethyl acetate, methanol and concentrated aqueous ammonia in a ratio of 20:4:1 by volume.

5.4 g of 1,3-dimethyl-4-($\gamma$-bromo-propyloxy)-uracil were obtained, representing a yield of 25%. The substance, after recyrstallization from ethyl acetate had a melting point of 113°-115° C.

1,3,5-Trimethyl-4-chloro-uracil, which was used as the starting material in Example 14, may be produced by the following method:

6.1 ml 89% phosphoric acid was added dropwise to 92 ml phosphorous oxychloride with stirring. When the formation of gas was terminated, 34 g (0.2 mole) 1,3,5-trimethyl-barbituric acid were added to the reaction mixture, followed by boiling under reflux for 2 hours. Thereafter, excess phosphorus oxychloride was distilled off in vacuo. The residue was poured onto ice, resulting in an increase of the temperature to about 90°-100° C. The crystals, precipitating on cooling of the mixture, were filtered off by suction. The remainder of the product was recovered from the filtrate by extraction with chloroform. After recrystallization from water, 23 g 1,3,5-trimethyl-4-chloro-uracil, having a melting point of 135° C, were obtained, representing a yield of 61%. Using in the just described method 1,3-dimethyl-5-n-butyl-barbituric acid as the starting material instead of the 1,3,5-trimethyl-barbituric acid, 1,3-dimethyl-4-chloro-5-n-butyl-uracil was obtained in a yield of 45%. This substance had a melting point of 59°-60° C and was used as the starting material in the method of Example 15.

1-n-Butyl-4-chloro-uracil which was used as the starting material in the method of Example 25, may be produced in the following manner:

To a solution of 23 g (1g-atom) sodium metal in 500 ml absolute ethanol were added at room temperature 35 g (0.3 mole) butyl-urea and 48 g (0.3 mole) malonic acid-diethylester. The alcohol was then distilled off in an oil bath held at 120° C and the residue maintained at this temperature for about 16 hours. The residue was then cooled and dissolved in about 300 ml water, stirred with activated carbon and the solution filtered. The clear filtrate was acidified by the addition of concentrated hydrochloric acid to produce 38 g 1-butyl-barbituric acid, representing a yield of 68%. The substance had, after recrystallization from benzene, a melting point of 107°–108° C.

10 g (0.055 mole) 1-butyl-barbituric acid were boiled for 3 hours under reflux with 110 ml phosphorus oxychloride and 7.7 ml 89% phosphoric acid. The excess phosphorus oxychloride was then distilled off and ice water and chloroform were given to the residue. The chloroform phase was separated, dried and the chloroform evaporated. 8.2 g 1-butyl-4-chloro-uracil were obtained, representing a yield of 73%. The substance, recrystallized from benzene, had a melting point of 187°–189° C.

1-Cyclohexyl-4-chloro-uracil, which was used as the starting material in Example 24, may be produced by the following method:

16 g (0.075mole) 1-cyclohexyl-barbituric acid were stirred for 16 hours at 70° C with 150 ml phosphorus oxychloride and 10.5 ml 89% phosphoric acid. Thereafter, the excess phosphorus oxychloride was distilled off at 70° C in vacuo. To the cooled residue was given, with stirring, ice water and chloroform, the chloroform phase was separated and the chloroform evaporated. The residue was chromatographically purified in a stationary column of silica gel "neutral" (Merck A.G.) having particle size of 0.02 to 0.5 mm. The flow agent was a mixture of chloroform and ether in a ratio of 6:1 by volume. 12 g 1:cyclohexyl-4-chloro-uracil were obtained, representing a yield of 70%. After recrystallization from ethanol, the substance had a melting point of 222°–224° C.

1-Phenyl-4-chloro-uracil and 3-phenyl-4-chloro-uracil, which were used as the starting materials in Examples 29 and 30, respectively, may be produced by the following method:

41.0 g (0.2 mole) 1-phenyl-barbituric acid were boiled for 3 hours under reflux with 400 ml phosphorus oxychloride and 28 ml 89% phosphoric acid. The excess phosphorus oxychloride was then removed in vacuo and the residue was treated with 1 liter ice water. The crystalline precipitate was thereafter filtered off by suction and washed with water, the filter residue was dissolved in 1 liter saturated sodium bicarbonate solution and 1 liter chloroform with subsequent separation of the phases into a chloroform phase and an aqueous phase. The chloroform was evaporated from the chloroform phase, the residue consisted of 11.8 g 3-phenyl-4-chloro-uracil, representing a yield of 26%. Recrystallized from ethanol, the substance had a melting point of 256° C. To the aqueous phase were added 1.5 liter chloroform and 150 ml methanol. The mixture was acidified by the addition of sufficient 2 n hydrochloric acid. In this manner, 13.8 g 1-phenyl-4-chloro-uracil were extracted and recovered, representing a yield of 31%. Recrystallization from ethanol resulted in a substance having a melting point of 265° C.

The starting materials used in Examples 35 to 38 may be produced in known manner by boiling of the correspondingly substituted phenylpiperazines with propyleneoxide in methanol, removal of the volatile reactants and solvents in vacuo and recrystallization of the residue. The reaction mechanism is as follows:

| Starting material of Example No. | Z | Melting point | Yield |
|---|---|---|---|
| 35 | o-OCH$_3$ | 66° C | 95% |
| 36 | H | 72–74° C | 98% |
| 37 | p-CH$_3$ | 117–119° C | 97% |
| 38 | p-Cl | 134–136° C | 55% |

EXAMPLE 61

1,3-Dimethyl-4-([4-(o-tolyl)-piperazinyl-(1)]-propylamino)-5-nitroso-uracil

The nitroso substituent is introduced into 1,3-dimethyl-4-(-[4-(c-tolyl)-piperazinyl-(1)]-propylamino-5-nitroso-uracil (obtained in example 12) by adding dropwise 10 ml of a 18% methanolic hydrochloric acid solution to 3.7 g. (0.01 mole) of the starting uracil and 3 ml of I-amylnitrite in 20 ml of chloroform and 10 ml of acetone. When a nearly white final precipitate is formed, after the color of the solution changed from light yellow to red and a precipitate was formed, the addition is stopped. The precipitate is separated by suction. The residue is washed with some acetone and ether. The product (5g) is obtained in 97% yield (of theory); its M.P. is 142°–145° C, with decomposition.

EXAMPLE 62

1,3-Dimethyl-[4-(gamma - (o-methoxyphenyl)-piperazinyl-(1) ] propylamino)-uracil There are heated 250 g (1 mole) of N-orthomethoxyphenyl)-N'-(gamma-aminopropyl)-piperazine in 750 ml of water to 90°–100° C and there is added while stirring dropwise 88 g (0.5 mole) of 1,3-dimethyl-4-chloruracil. Thereafter, there is added at 90°–100° C as a single portion, a further 91 g (0.52 mole) of 1,3-dimethyl-4-chloruracil.

After stirring for about an additional 10 minutes at 90°–100° C, there is added portion-wise 88 g (1.05 mole) of solid sodium bicarbonate, whereupon active foaming takes place initially. When the addition is terminated stirring is continued for about 10-15 minutes at 90°–100° C to promote the completeness of the reaction.

1,3-Dimethyl-[4-(gamma-(o-methoxyphenyl)-piperazinyl-(1)]-Propylamino)-uracil occurs then as an oil-like consistency, as the half-ester. There is then slowly added to the hot reaction mixture enough ethanol (about 0.4 to 0.5 liter) until a clear solution is obtained. The ethanol refluxes. The clear solution can be sucked off hot. It is allowed to cool slowly, while stirring to 20-20° C. The solution is seeded with some crystalline 1,3-dimethyl-4[4-(gamma (o-methoxyphenyl)-piperazinyl-)1)]-propylamino)-uracil. To promote the completeness of the crystallization there is added dropwise about 1.2 liter of water over 1 hour, about 20 minutes after seeding. After about 30 minutes complete precipitation has occurred, the liquid is sucked off, and the precipitate is washed with 0.6 to 0.8 liter of water.

Since the compound is readily soluble in aqueous acetone, the precipitate is completely and carefully dried (until essentially free of water) at 70°–80° C under vacuum. Then, it is purified by boiling with 500 ml of acetone, while stirring for 30 minutes, then allowed to cool and separated by suction, then washed with 300 ml of acetone and dried. The yield is 300 to 320 g (about 80% of theory); M.P. 155°–157° C.

The above described procedure represents a highly favored method for preparing one of the most desirable uracils of the invention.

Water which was described herein above to be useful as a suitable solvent in the reaction, is suitable in those instances (but not exclusively in those instances) in embodiment (a) of the process wherein in formula II, $R^3$ is hydrogen, methyl or ethyl and X is amino; in embodiment (b) of the process wherein formula IV, $R^3$ is hydrogen, methyl or ethyl and formula V, X is amino.

The novel compounds of the invention and their pharmacologically acceptable salts with suitable inorganic or organic acids are useful chemicals which have biological properties on mammalians and hence are useful in therapy on humans.

The compounds of the invention lower the blood pressure, reduce the heart beat rate, inhibit and carotid sinus relaxation reflex, and block the blood pressure increasing effect of adrenaline and noradrenaline, intravenously administered to the despinalized rat. They have a sedative and analgesic effect and also effective antihistaminics.

The compounds of the invention, as defined generically above are useful for the purposes described as shown hereinafter for the representative piperazinyl-uracils.

The following Table II shows the effect of representative piperazinyl uracils of the invention on the blood pressure, heart rate and the carotid sinus relaxation reflex of the narcotized cat as compared with the effect of phentolamine.

Table II

Effect of the aryl-substituted piperazinyl uracils of the invention on the blood pressure, heart rate and carotid sinus relaxation reflex of the narcotized cat.

| Compound of Example No. | Lowering of the blood pressure by | | Heart rate | | Inhibition of the carotid sinus reflex by | |
|---|---|---|---|---|---|---|
| | 30% with mg/kg i.v. | 50% with mg/kg i.v. | lowered | increased | 30% with mg/kg i.v. | 50% with mg/kg i.v. |
| 4 | 0.14 | 0.65 | + | − | 0.03 | 0.16 |
| 9 | 0.03 | 0.14 | − | − | 0.17 | 0.26 |
| 12 | 0.41 | 2.4 | + | − | | |
| 16 | 0.21 | 1.0 | − | − | 0.60 | 2.0 |
| 18 | 0.15 | >0.5 | − | − | 0.13 | 1.1 |
| 20 | 0.05 | 0.15 | − | − | 0.06 | 0.15 |
| Phentolamin | 0.1 | 0.7 | − | + | 0.1 | 0.5 |

Table III shows the effect of representative piperazinyl uracils of the invention on the blood pressure and on the heart beat rate of the narcotized rat and the influence on the blood pressure increasing effect of 0.001 mg/kg i.v. of adrenaline and noradrenaline on the despinalized rat, as compared to the corresponding effects of phentolamine.

Table III

| Compound of Example No. | $LD_{50}$ (median lethal dose) in the mouse | Rat narcotized | | | Despinalized rat 50% inhibition of the press. effect after i.v. administration of | |
|---|---|---|---|---|---|---|
| | | lowering of the blood pressure by 30% by | heart rate | | adrenaline with mg/kg i.v. | noradrenaline with mg/kg i.v. |
| | | | lowered | increased | | |
| 1 | 200 | 2.9 | − | − | 1.45 | − |
| 3 | 430 | 1.4 | + | − | 2.1 | − |
| 4 | 400 | 0.71 | + | − | 0.36 | 1.9 |
| 5 | 250 | 0.36 | + | − | 0.24 | − |
| 9 | 400 | >3.4 | − | − | 0.15 | − |
| 11 | 120 | 0.48 | + | − | 1.0 | >2.5 |
| 12 | 70 | 1.0 | + | − | 0.45 | 2.5 |
| 13 | 70 | >3.4 | + | − | >2.5 | − |
| 14 | 140 | 0.13 | + | − | 0.045 | 1.2 |
| 15 | 130 | 0.36 | + | − | 0.028 | 2.8 |
| 16 | 600 | 1.6 | − | + | 0.17 | − |
| 17 | 220 | 3.0 | − | + | 0.16 | 2.3 |
| 20 | 500 | 0.11 | + | − | 0.045 | 1.6 |
| 61 | 600 | 0.5 | + | − | 0.39 | 3.7 |
| Phentolamin | 200 | 0.63 | − | + | 0.047 | 0.18 |

Phentolamine, 2-[N'-p-tolyl-N'-(m-hydroxyphenyl)-aminomethyl]-2-imidiozoline is a recognized vasodepressor agent specifically inhibiting the stimulating effect of adrenaline and noradrenaline, typical alpha-blocking agent.

Tables II and III show that the typical piperazinyl uracils of the invention have a more pronounced lowering effect on the blood pressure and at the same time a lowr toxicity than phentolamine. The inhibition of the carotid sinus reflex, caused by the piperazine uracils of the invention takes place at lower doses than the spontaneous lowering of the blood pressure in the cat. This is evidence that the compounds of the invention inhibit the central blood pressure increasing mechanism of the circulatory system.

Chlordiazepoxyde has been used for a variety of conditions involving anxiety, as a sedative and as hypnotic, also as a sedative. Meprobate likewise has been used for such uses. The compounds of the invention likewise exhibit such properties.

The centrally inhibiting effect of the piperazinyl uracils of the invention in the mouse are apparent from Table IV. A comparison between the doses which affect the circulation and those which are centrally inhibiting shows that the effect on the blood circulatory system take place preferentially. The selective action of the compounds of the invention on the central blood pressure mechanism can be used advantageously in human therapy in the treatment of hypertonic diseases. The compounds of the invention represent a new type of antihypertensive pharmaceuticals which is not comparable in its mechanism with conventional available hypertonics.

Table IV
Central effects in the mouse

| Compound of Example No. | a $PD_{50}$ mg/kg i.p. | b $SD_{50}$ mg/kg oral | c % Inhibition of the motility in the tread wheel by | | d % prolongation of sleep induced by hexobarbital by 15 mg/kg i.p. |
|---|---|---|---|---|---|
| | | | 12 mg/kg i.p. | 25 mg/kg i.p. | |
| 1 | 28 | 40 | — | 36 | 110 |
| 4 | 52 | 100 | — | 36 | 71 |
| 5 | 26 | 98 | — | 46 | 126 |
| 9 | 12 | 30 | — | 79 | 140 |
| 11 | 11 | 70 | 22 | — | 130 |
| 12 | 26 | 87 | 42 | — | 49 |
| 14 | 12 | 90 | — | 21 | 152 |
| 20 | 34 | 80 | — | 42 | 62 |
| Chlordiazepoxyde | 38 | 8 | — | 30 | 324 |
| Meprobamate | 95 | 300 | — | +28 | 18 |

Explanation of Table IV.

$a$ = Dose, at which an average of 50% of the mice fall from a rotating rod.

$b$ = Dose, at which at an average 50% of the mice show the following symptoms: inhibition of the spontaneous motility, sadation, muscle relaxation, loss of gripping and holding ability on a horizontal wire net.

$c$ = average inhibition of the running activity in percent of mice, to which was administered 5 mg/kg d-amphetamine-sulfate (compared with mice, which were administered d-amphetamine-sulfate only) during 180 minutes.

$d$ = Percent prolongation of the duration of sleep of mice, which were administered 75 mg/kg hexobarbital, compared with the sleep duration of controls.

Aminopyrine (aminophenazone, pyramidone) have been used for analgesia and for their anti-inflammatory effects.

Tables V and VI demonstrated the analgesic effect and the antihistamine effect of the piperazinyl uracils of the invention as compared with the effects of aminophenazone and piprinhydrinate, respectively. The analgesic effect was thereby determined as the delay in the reaction upon thermal stimulation of the tail of the mouse.

Table V

| Compound of Example No. | Analgesic effect in the mouse Retardation of the defense reaction upon thermal stimulation of the tail of the mouse by 25% by mg/kg orally administered |
|---|---|
| 1 | 5.0 |
| 3 | 7.0 |
| 4 | 2.4 |
| 5 | 9.0 |
| 9 | 10.0 |
| 12 | 6.5 |
| 16 | 10.0 |

Table V-continued

| Compound of Example No. | Analgesic effect in the mouse Retardation of the defense reaction upon thermal stimulation of the tail of the mouse by 25% by mg/kg orally administered |
|---|---|
| Aminophenazone | 140.0 |

Table VI

| Compound of Example No. | Antihistamine effect 50% inhibition of the histamine spasm of the isolated small intestine of the guinea pig by g/ml |
|---|---|
| 7 | $2 \times 10^{-8}$ |
| 12 | $3 \times 10^{-8}$ |
| 13 | $1 \times 10^{-8}$ |
| Piprinhydrinate | $1.5 \times 10^{-8}$ |

For additional details regarding the above-described and other applications, reference is made to *The Pharmacological Basis of Therapeutics* (3rd Ed.), Goodman & Gilman, The Macmillan Company, New York, 1968, especially Section II, chapter 17, Section V, chapter 20, Section VI, chapter 34.

Clinical tests were conducted with the 1,3-dimethyl-4-(γ-[4(o-methoxyphenyl)-piperazinyl-(1)]-propylamino)-uracil on two female and three male patients, with doses of 10, 20, 40 and 60 mg orally administered. The compound was found to have excellent compatibility, caused no adverse effect on perception and other sensory functions and produced a statistically significant lowering of the systolic and diastolic blood pressure.

Figure 1:
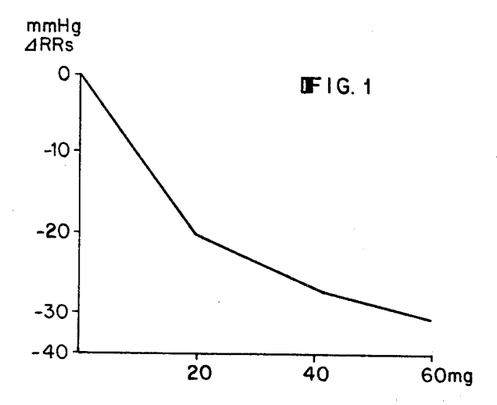
Figure 2:
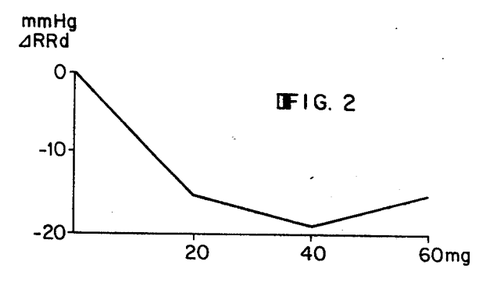

Attached Diagrams 1 and 2 show the changes of the blood pressure under the effect of various doses of 1,3-dimethyl-4-(γ-[4-(o-methoxyphenyl)-piperazinyl-(1)]-propylamino)-uracil. Diagram 1 shows the changes of the systolic blood pressure under the effect of doses from 0 to 60 mg of the uracil compound in a patient having an average systolic blood pressure ($RR_s$) of 171.9 mm Hg. Diagram 2 shows the changes of the diastolic blood pressure with the same doses of the uracil compound at an average starting diastolic blood pressure ($RR_d$) of 95.3 mm Hg plotted against the dose of the uracil compound. These diagrams show clearly, that the blood pressure is progressively lowered in response to an increasing dose of the uracil compound. The difference in the effect of a dose of 20 mg and a dose of 40 mg was statistically confirmed.

The pharmacological and clinical tests show, that piperazinyl uracils of the invention and their pharmacologically acceptable salts with pharmacologically acceptable acids are valuable medicaments, especially for the treatment of hypertonicity.

The invention is therefore also concerned with medicaments or drugs, which are characterized by comprising one or more of the compounds of the invention or of the pharmacologically acceptable salts thereof, in combination with a pharmaceutical acceptable carrier material and, if desired, with the usual auxiliary additives.

Standard modes of administration are contemplated. The new medicaments may, for instance, be formulated as dragees, tablets, capsules, suppositories, solutions for injection, or as syrup. The single dose is, in the case of oral administration, generally in the range from 5 to 100 mg, preferably 20 to 60 mg of the effective piperazinyl uracil compound; in the case of intramuscular administration the single dose is generally from 1 to 50 mg, preferably from 10 to 20 mg of the piperazinyl uracil substance.

In the case of intravenous administration the single dose of generally from 1 to 30 mg, preferably from 5 to 15 mg of the piperazinyl uracil substance. The single doses of this magnitude may be administered several times per day. Oral administration is preferred.

The following are two illustrations of the composition of dragees and injection solution in ampules in accordance with the present invention.

Dragées

Components:

1350.0 g 1,3-dimethyl-4-(γ-[4-(o-methoxypheny)-piperazinyl-(1)]-propylamino)-uracil
1125.0 g corn starch
1372.5 g lactose
22.5 g "Aerosil"
22.5 g gelatin
135.0 g talc
22.5 g magnesium stearate The uracil substance, the corn starch, the lactose and the "Aerosil" are mixed. The mixture is sifted and granulated, together with the gelatine and 750 ml water through a sieve of 1.5 mm mesh size. After drying at 40° C, the talc and the magnesium stearate are added and mixed in. The mixture is then pressed to dragée centers of 8 mm diameter and 180 mg weight. The dragée centers are then coated by the use of a rapid coating suspension of conventional composition to a weight of 220 mg. Each dragée contains 60 mg of the effective uracil compound.

Ampules

Components

10.0 g 1,3-dimethyl-4-(γ-[4-(o-methoxyphenyl)-piperazinyl-(1)]-propylamino)-uracil
240.0 ml 0.1 n hydrochloric acid, aqueous
7.5 g sodium chloride
filled up with water to 1000 ml.

The uracil compound is suspended in 500 ml water, the hydrochloric acid added thereto and the mixture stirred to dissolve the uracil compound. To the solution there is added the sodium chloride, and water to make one liter. The solution is filtered through a finely porous membrane filter layer ("Seitz 1121") and the filtrate filled into colorless 1 ml glass ampules, which are subsequently sterilized for 1 hour at 100° C. The injection solution made in this manner has a $p_H$ of 6.0. It is useful in cardiovascular therapy.

The compounds of the invention wherein Z is linked in the ortho position like o-alkoxy, or o-alkyl or where z is hydrogen have especially enhanced effect on the blood circulatory system and as sedatives or analgesics, whereas those compounds wherein Z is in the para position are especially noteworthy for their antihistaminic effect.

We claim:

1. The method of causing a lowering of the blood pressure, causing an analgesic effect, antihistiminic effect or a sedative effect in a warm-blooded animal which comprises administering in a therapeutically effective dose, a pharmaceutical composition comprising a compound of the formula:

wherein
$R^1$ and $R^2$ each is hydrogen, alkyl or alkenyl of 1 to 6 carbon atoms, cycloalkyl of 5 to 6 carbon atoms, or phenyl;
$R^3$ is hydrogen, alkyl or alkenyl of 1 to 6 carbon atoms, cycloalkyl of 5 to 6 carbon atoms, chlorine or bromine, phenyl, aralkyl, wherein the alkyl is of 1 to 3 carbon atoms, nitro, nitroso, amino, alkylamino of 1 to 3 carbon atoms, dialkylamino wherein each of the alkyl groups contain 1 to 3 carbon atoms, alkanoylamino of 1 to 4 carbon atoms, formyl, ethoxycarbonylamino, thiocyanato, $COCH_3$ or $CONHC_6H_5$;
X is —NH—, —NC$_2$H$_5$—, —O— or —S—;
A is —CH$_2$—CH$_2$CH$_2$—, —CH(CH$_3$)—CH$_2$— or —CH$_2$— CH(CH$_3$);
Z is hydrogen, a methyl group, one or two methoxy groups or an ethoxy group, a chlorine atom and
Y is hydrogen, and the pharmaceutically acceptable salts of these compounds, in mixture with a pharmaceutically acceptable carrier.

2. The method of claim 1 wherein the administration is to humans.

3. The method of claim 2 of causing a lowering of the blood pressure.

4. The method of claim 2 of causing an analgesic effect.

5. The method of claim 2 of causing an antiinflammatory effect.

6. The method of claim 2 of causing sedation.

7. The method of claim 3 wherein the substituent Z is in the ortho-position or is hydrogen.

8. The method of claim 7 wherein the substituent Z is in the para-position.

9. The method of claim 6 wherein the substituent Z is in the ortho-position or is hydrogen.

10. The method of claim 4 wherein the substituent Z is in the ortho-position or is hydrogen.

11. The method of claim 3 wherein the compound is 1,3-dimethyl-4-(gamma-[-0-methoxyphenyl)-piperazinyl-(1)]-propylamino)-uracil.

12. A pharmaceutical composition for use in mammals to cause: a lowering of blood pressure, an analgesic, a sedative, or an histiminic effect, comprising, in a therapeutically effective amount to cause such effect, a compound of the general formula wherein
R¹ and R₂ each is hydrogen, alkyl or alkenyl of 1 to 6 atoms, cycloalkyl of 5 to 6 carbon atoms, or phenyl;
R³ is hydrogen, alkyl or alkenyl of 1 to 6 carbon atoms, cycloalkyl of 5 to 6 carbon atoms, chlorine or bromine, phenyl, benzylalkyl wherein the alkyl is of 1 to 3 carbon atoms, nitro, nitroso, amino, alkylamino of 1 to 3 carbon atoms, dialkylamino wherein each of the alkyl groups contain 1 to 3 carbon atoms, alkanoylamino of 1 to 4 carbon atoms, formyl, ethoxycarbonylamino, thiocyanato, $COCH_3$ or $CONHC_6H_5$;
X is $-NH-$, $-NC_2H_5-$, $-O-$ or $-S-$;
A is $-CH_2-CH_2-CH_2-$, $-CH(CH_3)-CH_2-$ or $-CH_2-CH(CH_3)$;
Z is hydrogen, a methyl group, one or two methoxy groups or an ethoxy group, a chlorine atom and
Y is hydrogen, and the pharmacetucally acceptable salts of these compounds in mixture with a pharmaceutically acceptable carrier.

13. The pharmaceutical composition of claim 12 in a therapeutically effective dosage of from about 1 to 100 mg.

14. The pharmaceutical composition of claim 13 wherein the dosage is of about 5 to 100 mg, especially suited for oral administration.

15. The pharmaceutical composition of claim 12 wherein the dosage is from about 1 to 50 mg, especially suited for intramuscular administration.

16. The pharmaceutical composition of claim 12 wherein the dosage is from about 1 to 30 mg especially suited for intravenous administration.

17. The composition of claim 12 wherein the compound is 1,3-dimethyl-4-(gamma-[4-(o-methoxyphenyl)-piperazinyl-(1)]-propylamino)[4-bromo]-uracil.

18. The composition of claim 12 wherein the compound is 1,3-dimethyl-4-(gamma-[4-o-methoxyphenyl)-piperazinyl-(1)]-propylamino)-5-propionylamino-uracil.

19. The composition of claim 12 wherein the compound is 1,3-dimethyl-4-(1-methyl-2[4(ortho-methoxyphenyl-piperazinyl-(1)]-ethyloxy)uracil.

20. The composition of claim 12 wherein the compound is in the form of its salt with a pharmaceutically acceptable organic or inorganic acid.

* * * * *